US009517083B2

(12) United States Patent
Sherry et al.

(10) Patent No.: US 9,517,083 B2
(45) Date of Patent: Dec. 13, 2016

(54) APPARATUS FOR TREATING AN ORGAN AND RELATED METHODS OF USE

(75) Inventors: John Sherry, Needham, MA (US); Sandra Nagale, Lowell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 287 days.

(21) Appl. No.: 13/599,916

(22) Filed: Aug. 30, 2012

(65) Prior Publication Data

US 2013/0072855 A1 Mar. 21, 2013

Related U.S. Application Data

(60) Provisional application No. 61/535,710, filed on Sep. 16, 2011, provisional application No. 61/677,590, filed on Jul. 31, 2012.

(51) Int. Cl.
  *A61B 17/34* (2006.01)
  *A61B 17/00* (2006.01)
  *A61B 17/32* (2006.01)

(52) U.S. Cl.
  CPC .. *A61B 17/3478* (2013.01); *A61B 2017/00743* (2013.01); *A61B 2017/00805* (2013.01); *A61B 2017/320044* (2013.01); *A61B 2090/3933* (2016.02); *A61M 2210/1078* (2013.01); *A61M 2210/1085* (2013.01); *A61M 2210/1089* (2013.01)

(58) Field of Classification Search
  CPC ............. A61M 2210/1078; A61M 2210/1085; A61M 2210/1089; A61M 5/3298; A61M 5/3297; A61M 5/3295; A61B 2017/00743; A61B 2017/00805

USPC ................. 604/500, 503, 506, 511, 517, 57, 523,604/502, 96.01, 104
See application file for complete search history.

(56) References Cited

U.S. PATENT DOCUMENTS

| 6,428,802 B1 * | 8/2002 | Atala ................. A61L 27/3804 424/423 |
| 7,955,316 B2 * | 6/2011 | Weitzner et al. ............. 604/528 |
| 2006/0070631 A1 * | 4/2006 | Scopton et al. ............. 128/898 |

(Continued)

FOREIGN PATENT DOCUMENTS

WO WO 2012013246 A1 * 2/2012

OTHER PUBLICATIONS

Wang, K., Prasad, G., & Tian, J. (2010) Endoscopic mucosal resection and endoscopic submucosal. Curr Opin Gastroenterol., 26, 453-458.*

(Continued)

*Primary Examiner* — Imani Hayman
*Assistant Examiner* — Nilay Shah
(74) *Attorney, Agent, or Firm* — Bookoff McAndrews, PLLC

(57) ABSTRACT

A method of treatment may include advancing a medical device to a wall of an organ having a plurality of layers of tissue. The medical device may include an elongate tube having a proximal end and a distal end, a lumen extending therebetween, and an injector disposed within the lumen. The injector may be configured to deliver a substance to a location between first and second layers of tissue of the plurality of layers of tissue within the organ wall. In addition, the method may further include delivering the substance to the location, wherein, when delivered, the substance is configured to spatially separate a portion of the first and second layers of the tissue.

17 Claims, 5 Drawing Sheets

(56) References Cited

U.S. PATENT DOCUMENTS

| | | | |
|---|---|---|---|
| 2008/0051627 A1* | 2/2008 | Raju | 600/104 |
| 2008/0125804 A1* | 5/2008 | Gostout | 606/192 |
| 2008/0154228 A1* | 6/2008 | Ortiz et al. | 604/500 |
| 2009/0018603 A1* | 1/2009 | Mitelberg et al. | 607/40 |
| 2010/0056989 A1* | 3/2010 | McKay | A61B 17/3478 604/28 |
| 2011/0124765 A1* | 5/2011 | Yang et al. | 522/87 |

OTHER PUBLICATIONS

Lippincott Williams & Wilkins. (2007). Straight A's in anatomy & physiology. Philadelphia: Lippincott Williams & Wilkins.*

Andersson, K., Arner, A., (2004) Urinary Bladder Contraction and Relaxation: Physiology and Pathophysiology. Physiol Rev. 84, 935-986.*

Chess-Williams, R., (2002) Muscarinic receptors of the urinary bladder: detrusor, urothelial and prejunctional., Autonomic & Autacoid Pharmacology. 22, 133-145.*

Canning, B. J., Spina, D., & Baron, R. (2009). Sensory nerves. Dordrecht: Springer.*

SEER Training Modules. (Jun. 23, 2009). Retrieved Nov. 20, 2014, from http://training.seer.cancer.gov/bladder/anatomy/layers.html.*

"Histology Fact Sheet: Urinary Bladder." Histology-World! Histology Fact Sheet-Urinary Bladder. Web. Jun. 2, 2016. <http://www.histology-world.com/factsheets/bladder1.htm>.*

Lin, Yung-Chang, and Shi-Ming Tu. "Bladder Cancer." Physicians Practice (2005): 1-13. Web. Jun. 1, 2016.*

"Core Technology," retrieved from Contura website at http://www.contura.com/products/core-technology on Dec. 28, 2012 (2 pages).

Hillel, Alexander T. et al., "Photoactivated Composite Biomaterial for Soft Tissue Restoration in Rodents and in Humans," *Science Translational Medicine*, vol. 3, Iss. 93, p. 93ra67 (2011) (13 pages).

Karajanagi, Sandeep S. et al., "Assessment of Canine Vocal Fold Function After Injection of a New Biomaterial Designed to Treat Phonatory Mucosal Scarring," Annals of Otology, Rhinology & Laryngology, vol. 120, pp. 175-184 (2011), Abstract (1 page).

"Products: Tissue Repair," retrieved from Fidia website at http://www.fidiapharma.com/files/index.cfm?id_rst=137 on Dec. 28, 2012 (3 pages).

Apostolidis et al., "Proposed Mechanism for the Efficacy of Injected Botulinum Toxin in the Treatment of Human Detrusor Overactivity," European Urology 49 (2006) pp. 644-650.

* cited by examiner

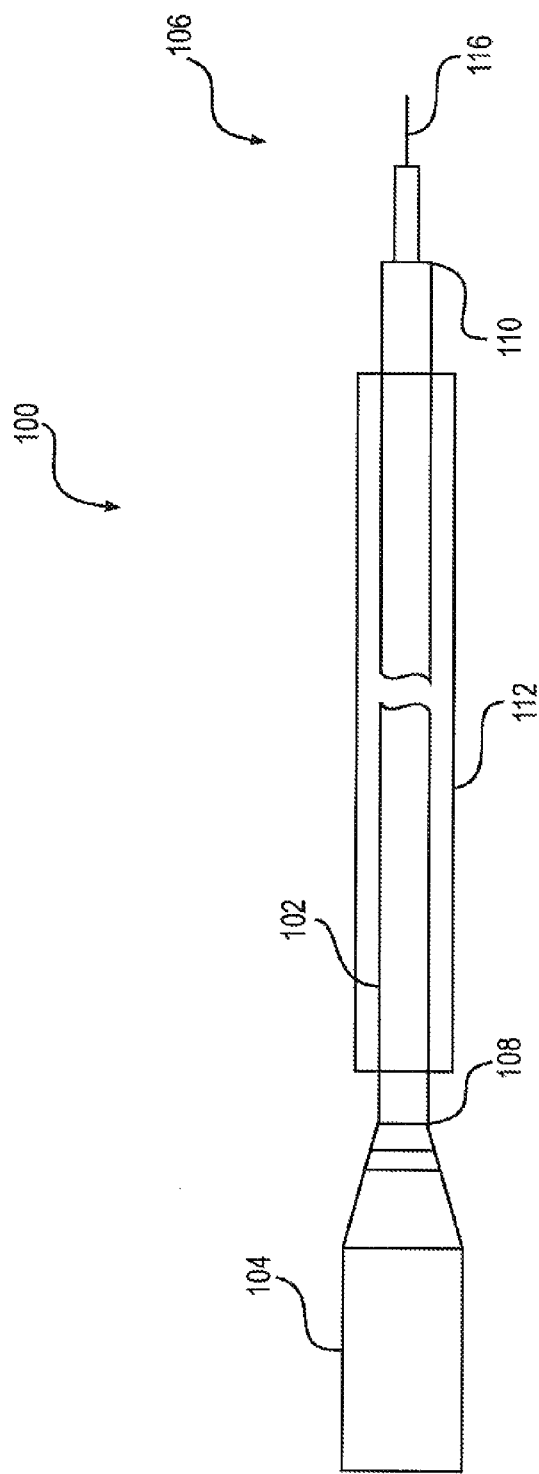
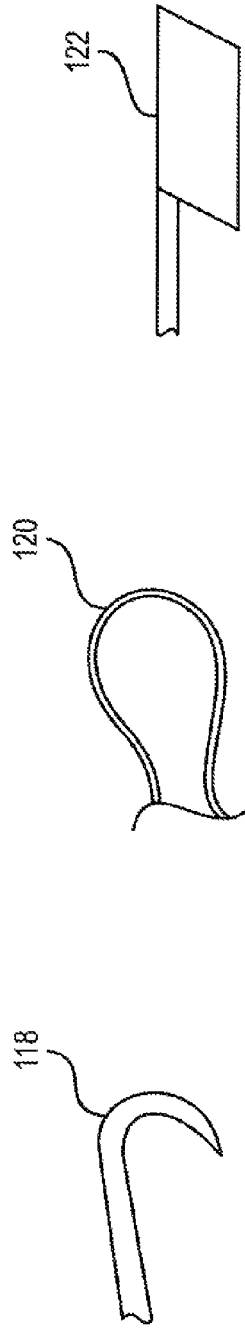
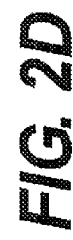

APPARATUS FOR TREATING AN ORGAN AND RELATED METHODS OF USE

CROSS-REFERENCE TO RELATED APPLICATIONS

This patent application claims the benefits of priority under 35 U.S.C. §119-120 to U.S. Provisional Application No. 61/535,710, filed on Sep. 16, 2011, and U.S. Provisional Application No. 61/677,590, filed on Jul. 31, 2012, for which the entirety of each is incorporated herein by reference.

FIELD OF THE INVENTION

Embodiments of this disclosure relate generally to medical devices and procedures. In particular, embodiments of the present disclosure relate to medical devices and procedures for treating a bladder within a patient.

BACKGROUND OF THE INVENTION

Overactive Bladder (OAB) is a urological condition that affects approximately 50 million patients worldwide. A patient suffering from OAB typically experiences sudden yet frequent and unstoppable urges to urinate, even though the bladder may only contain a small amount of urine. This condition is usually associated with frequent and spontaneous contractions of the detrusor muscle, which is located in the bladder wall and surrounds the bladder.

The etiology of OAB is unclear, and indeed there may be multiple possible causes. OAB, however, is often associated with detrusor muscle overactivity (i.e., frequent and spontaneous contractions of the detrusor muscle). These frequent contractions may fuse into a global and sustained contraction resulting in an urge to urinate. A malfunctioning detrusor muscle may cause overactive bladder. Studies suggest that, in comparison with healthy bladders, overactive bladders may exhibit localized changes in detrusor muscle morphology. These changes may originate from defects on cellular and multi-cellular levels and changes in the nervous system. Such nervous system changes may be correlated to observed local pathological changes in the muscle (e.g., patchy denervation, increased amount of connective tissue between muscle bundles), which may contribute to the abnormal function of the detrusor muscle.

Identifiable underlying causes of OAB may include the following: nerve damage caused by abdominal trauma, pelvic trauma, or surgery; bladder stones; drug side effects; and neurological disease (e.g., multiple sclerosis, Parkinson's disease, stroke, spinal cord lesions).

Recent evidence suggests that the detrusor muscle may be triggered by chemicals released from the bladder wall when the wall experiences stimulation, including, but not limited to, stretching of the bladder wall or the presence of potassium or a specific pH level, all of which may be associated with increasing accumulation of urine. The released chemicals may include adenosine triphosphate, prostaglandins, nitric oxide, and acetylcholine. The release of these chemicals may be linked to over-expression of multiple receptors (muscarinic and cholinergic receptors, TRPV, etc.).

Current therapies for OAB may include a variety of approaches. Non-invasive procedures include first-line behavioral and medical therapies that may employ a class of systemic drugs called anticholinergics. For patients who do not react well to drugs, invasive procedures, such as neural stimulation or surgery, may be more effective. Both invasive and non-invasive treatments typically target overall bladder function and do not address local or anatomical abnormalities. Recent studies, however, suggest that abnormal activity may originate from one or more distinct anatomical areas of the bladder such as the dome, internal sphincter, or trigone. Therefore, there exists a need for methods of treatment or medical devices capable of identifying and providing therapy to specific areas of the bladder.

SUMMARY OF THE EMBODIMENTS

Embodiments of the disclosure include a method of treatment. Various embodiments of the disclosure may include one or more of the following aspects.

In accordance with an aspect of the present disclosure, a method of treatment may include advancing a medical device to a wall of an organ having a plurality of layers of tissue. The medical device may include an elongate tube having a proximal end and a distal end, a lumen extending therebetween, and an injector disposed within the lumen. The injector may be configured to deliver a substance to a location between first and second layers of tissue of the plurality of layers of tissue within the organ wall. In addition, the method may further include delivering the substance to the location, wherein, when delivered, the substance is configured to spatially separate a portion of the first and second layers of the tissue.

In various embodiments, the method may further include one or more of the following aspects: the method may further include extending the injector out of the lumen, wherein the injector is configured to pierce the organ wall; the method may further include applying suction to one of the first and second layers of tissue; the medical device may include an anchoring element for securing the needle relative to the organ wall; the medical device may include an expandable member configured to secure the medical device relative to the organ wall; the expandable member may be an inflatable balloon; the medical device may be robotically controlled; the organ may be a bladder, the first layer may include a mucosal layer, and the second layer may include a submucosal layer; the submucosal layer may include a detrusor muscle; the organ may be a bladder and the first layer may be urothelium and the second layer may be one of a lamina propria and a muscular layer; the first and second layers may include nerves, the second layer including a greater number of nerves than the first layer, and the first layer may further include one of a muscarinic and a cholinergic receptor; the method may further include delivering a substance at a plurality of locations; the method may further include identifying a location of abnormality on the organ wall; the substance may include a fluid configured to cure into a solid; and the substance may be configured to deliver a drug over a period of time.

In accordance with another aspect of the present disclosure, a method of separating one or more of a plurality of layers of tissue within a wall of a bladder may include positioning a distal end of a medical device adjacent the wall of the bladder. The medical device may include an elongate tube having a proximal end and a distal end and a lumen extending there between. The medical device may also include an injector disposed within the lumen of the elongate tube, the injector including a needle configured to pierce the wall of the bladder. The method may further include advancing the injector to a location within the wall of the bladder and delivering a substance between first and second layers of the wall of the bladder. When delivered, the substance may be configured to spatially separate a portion of the first and second layers of the wall of the bladder.

In various embodiments, the method may further include one or more of the following aspects: the method may further include resecting the spatially separated portion of at least one of the first and second layers of the wall of the bladder with a resection tool; the resection tool may include at least one of a hook, a snare, and a surgical blade; and the method may further include applying suction to one of the first and second layers.

Additional objects and advantages of the disclosure will be set forth in part in the description, which follows, and in part will be evident from the description, or may be learned by practice of the disclosed subject matter. The objects and advantages of the disclosed subject matter will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate certain exemplary embodiments of the present disclosure, and together with the description, serve to explain principles of the disclosure. Wherever possible, the same reference numbers will be used throughout the drawings to refer to the same or like parts.

FIG. 2A is an exemplary medical device for separating tissue layers, according to an embodiment of the present disclosure;

FIGS. 2B, 2C and 2D are exemplary tools for use with the medical device of FIG. 2A;

DESCRIPTION OF THE EMBODIMENTS

Reference will now be made in detail to the exemplary embodiments of the present disclosure described below and illustrated in the accompanying drawings. Wherever possible, the same reference numbers will be used throughout the drawings to refer to same or like parts.

While the present disclosure is described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the invention. Accordingly, the disclosure is not to be considered as limited by the foregoing or following descriptions.

Other features and advantages and potential uses of the present disclosure will become apparent to someone skilled in the art from the following description of the disclosure, which refers to the accompanying drawings.

Overview

Figure 1:
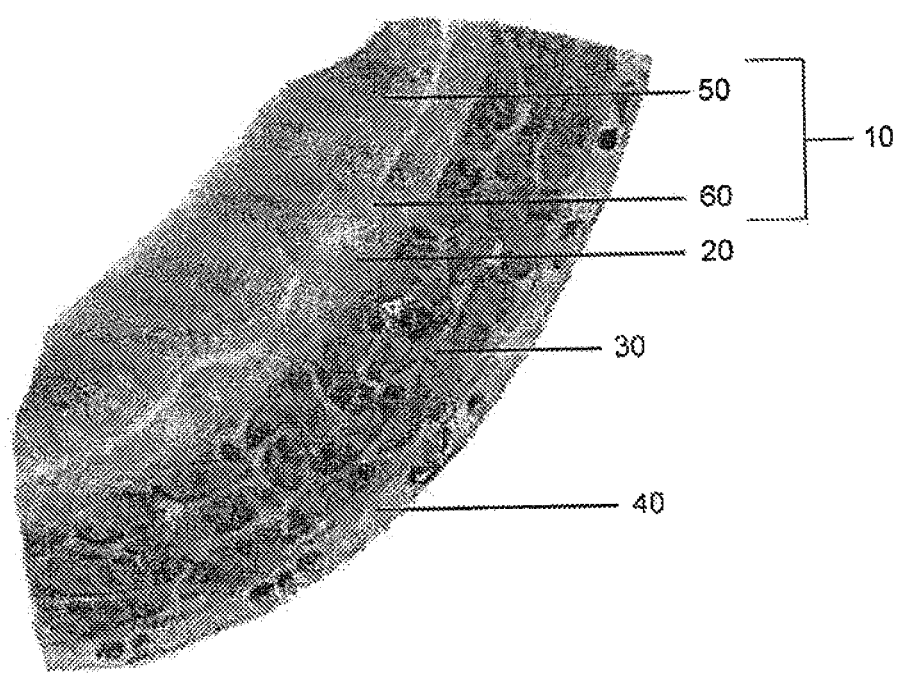
FIG. 1 schematically illustrates a bladder wall of a patient.

The urinary bladder is an organ for collecting and disposing of urine excreted from the kidneys. As shown in FIG. 1, the bladder includes a wall made up of three primary layer regions. Those regions, from inside out, include the mucosa 10 (mucosal layer or mucosal region), submucosa 20 (submucosal layer or submucosal region), and the muscularis, including the detrusor muscle 30. The external-most layer of the bladder includes the serosal layer 40. Typically, the urothelium 50 (also referred to as the epithelium), which surrounds the interior of the bladder, and lamina propria 60 layers make up mucosal region 10. It is these layers that typically perform the triggering function described above. Submucosal region 20 follows the mucosal region 10 and is typically densely packed with nerve fibers. Submucosal region 20 may include a greater number of nerves than mucosal region 10. The muscularis region follows submucosal region 20 and includes detrusor muscle 30. In a healthy bladder, urothelium 50, when subject to stimulation, such as stretching caused by urine accumulation, signals detrusor muscle 30 contractions. The signals are triggered by a variety of mechanical or chemical stimuli at urothelium 50, releasing compounds such as adenosine triphosphate (ATP), prostaglandin, nitric oxide (NO), and acetylcholine (Ach) molecules, and the like. An overactive bladder (OAB), on the other hand, exhibits changes in detrusor muscle 30 morphology, originating from defects on a cellular, multi-cellular, or nervous system level.

Embodiments of the present disclosure relate to methods and apparatus for treating urinary bladder overactivity. The disclosed embodiments include a hydro dissection procedure, which separates the signaling layers (e.g., urothelium 50 and/or lamina propria 60) from submucosal layers 20, including, but not limited to, muscular layer 10, by injecting a compound into certain areas of the urinary bladder wall. Separating mucosal layers 10 from submucosal layers 20 inhibits signal transduction to the neural layer by diluting/blocking secreted substances, thus modifying detrusor muscle 30 contraction. In particular, the present disclosure contemplates separating muscarinic and cholinergic receptors in urothelial 50 or mucosal layers 10, including at least urothelial 50, from submucosal layers 20. Since the muscarinic and cholinergic receptors trigger detrusor 30 contractions in response to detecting the presence of urine, physically separating them from submucosal region 20 is believed to affect the ability of those receptors to activate detrusor muscle 30. The injected substance may be saline or a similar inert compound, in the form of a fluid or gel, for example. The injected substance may also include agents or other materials, such as radiopaque materials, fillers, or healing promoters.

Following the separation of the above-noted tissue layers, embodiments of the present disclosure may further include resection and removal of the separated mucosal layer 10. That is, upon lifting mucosal layers 10, including at least urothelial layer 50 from submucosal layer 20, the lifted tissue may be dissected, i.e., cut and removed from remaining tissue portions as will be described in further detail below. It is also contemplated that layers could be resected and removed or dissected without separation of the above-noted tissue layers.

The following description focuses on techniques for treating OAB, but those in the art will understand that the same techniques may be employed in treating other organs. Such treatments may be useful for organs such as the esophagus, stomach, or intestines, colon, or the oral cavity, without departing from the scope of the present disclosure. Moreover, a variety of injecting devices, including electrical, mechanical, or pneumatic injectors, may be employed in the disclosed methods, operating under manual or automated computer control.

Exemplary Embodiments

FIG. 2A illustrates an exemplary medical device 100 for separating mucosal 10 and submucosal 20 regions according to an embodiment of the present disclosure. Medical device 100 may include a cystoscope, endoscope, or any suitable introducer configured for insertion into a body of a patient. Medical device 100 includes an elongate tube 102, a handle 104, and an injector device 106. Elongate tube 102 has a proximal end 108 and a distal end 110, those terms referring to positions or directions nearer to or farther from the user, respectively. Elongate tube 102 may include one or more lumens. In some embodiments, the lumen(s) of elongate tube 102 may be used to pass one or more tools to a target site within a patient's body. Such tools may include, e.g., biopsy devices, snares, suture needles, laser fibers, or suitable imaging devices. In particular, such tools may include a hook 118 (FIG. 2B), a snare 120 (FIG. 2C), and a blade 122 (FIG. 2D), as will be described in further detail below. Tools and devices may conduct energy, for example, RF energy or laser energy, to assist in a procedure. In addition, elongate tube 102 may include integrally-formed illumination and imaging devices, as well as sensing elements (e.g., sensors for pH, ions such as potassium, calcium, sodium, and biosensors for bio markers in urine, etc.). The imaging devices and sensing elements enable the detection of abnormalities in the bladder wall, which may then be followed by subsequent injection, resection, and tissue regrowth.

Elongate tube 102 extends from handle 104 to injector device 106 and advances injector device 106 into an operating position, as discussed below. Elongate tube 102 is hollow, with a cross-sectional configuration adapted for insertion in the lower urinary tract. In the illustrated embodiment, elongate tube 102 includes a generally circular cross-section, with a generally circular hollow interior opening. Further, elongate tube 102 is also adapted for flexible steering within bodily lumens, as understood in the art. In particular, distal end 110 of elongate tube 102 may be selectively steerable.

Elongate tube 102 may be formed from any suitable material having sufficient flexibility to traverse body cavities and tracts. Suitable materials may include synthetic plastics and polymers. Alternatively, materials, such as, stainless steel or the like, including super elastic or shape memory alloys, such as nitinol, have proved particularly suitable for such applications. The degree of flexibility imparted to elongate tube 102 can vary based on the particular application, ranging from highly flexible tubes adapted to be highly maneuverable, to tubes that are substantially rigid.

Medical device 100 may be enclosed in an outer sheath 112, which may surround elongate tube 102 and injector device 106 from the flexible tube's proximal end to the injector device's distal end. Sheath 112 preferably has the same cross-sectional shape as elongate tube 102 and fully covers elongate tube 102 and/or injector device 106. In this state, medical device 100 may be inserted into a body cavity or surgically advanced to the desired site. When medical device 100 is positioned at the desired location, sheath 112 may be pulled proximally or elongate tube 102 may be pushed distally so that injector device 106 extends out of the sheath's distal end into an operating state. The injector device's actuation described here may be carried out by any suitable actuation mechanism. For example, a pulling or pushing mechanism may be incorporated in handle 104, allowing the physician to deploy injector device 106 when required. For purposes of this disclosure, sheath 112 may be formed of material such as polyamide, polyurethane, rubber, PTFE, polyethylene, polytetrafluoroethylene, or any other suitable material.

Moreover, sheath 112 may include one or more lumens for passing suitable tools to a target site within a patient's body. These tools may include, e.g., biopsy devices, snares, resection devices, suture needles, imaging devices, sensors, and/or illumination devices. In some embodiments, sheath 112 may include integrally-formed illumination and imaging devices.

Injector device 106 of the illustrated embodiment may include a conventional needle, having a sharpened distal point and hollow interior. This device may be adapted for attachment to elongate tube 102 by conventional means, such as a screw attachment. If detachable, injector device 106 may be disposable. Alternatively, device 106 may be formed integrally with the remainder of the instrument. As illustrated, medical device 100 employs a single injector device 106, but it will be understood that multiple devices may be employed. For example, one embodiment may include multiple elongate tubes 102 carried within a sheath 112, each elongate tube 102 having its own injector device 106 and injector 116, allowing injection at multiple locations, as desired. Those in the art will understand that a range of alternatives could be brought to bear for alternate implementations of injector device 106. In other embodiments, for example, a single injector device 106 may include a plurality of injectors 116. For example, the device of FIG. 2A may include two or more injectors 116 instead of the single injector 116 shown. Additionally, device 106 may be capable of providing multiple injections with either a single injector or multiple injectors 116 and either at the same location or different locations.

Medical device 100 may include an expandable member for securing injector device 106 near the bladder wall. For example, the expandable member may be an inflatable balloon, which may be inflated once injector device 106 is extended out of elongate tube 102 for substance insertion. As known in the art, any suitable expandable member, including, e.g., a mechanical cage or foam, may be employed for securing medical device 100 near the bladder wall.

Additionally, injector 116 disclosed herein may include mechanical or electrical injectors. Different types of injectors 116 are well known in the art and will not be described in detail here. The substance, such as a hydrogel, radiopaque materials, fillers, or healing promoters, to be injected may be carried in a dispenser (not shown). Such a dispenser may be a part of injector 116 or may be present at the proximal end of elongate tube 102 near handle 104. As known in the art, the dispenser may be operated manually or under computer control to deliver the substance at the targeted area.

In some embodiments, medical device 100 may include a suction device at a distal end to assist in the lifting of layers (e.g., urothelium 50) associated with the mucosal region. For example, suction may be used to separate mucosal layer 10 and submucosal layer 20. The suction procedure may be followed by substance insertion in between the layers. The distal end of medical device 100 may also include integrated illumination and/or visualization optics (i.e., camera).

In addition, a portion of medical device 100 may include a coating. In one embodiment of the present disclosure, medical device 100 may be coated with an antibacterial material to inhibit bacterial growth on the surface of medical device 100. Alternatively, medical device 100 may be coated with a lubricious coating to facilitate insertion into, for example, the bladder and urethra. In some embodiments, medical device 100 may include radiopaque or sonoreflective markers, or may comprise radiopaque or sonoreflective materials, surfaces, and/or coatings, to locate medical device 100 inside the body lumens. Medical device 100 may further comprise a surface modified to reflect ultrasonic imaging by means of, e.g., bumps, dimples, grooves, ridges, coatings, or other suitable structures.

As noted above, elongate tube 102 may include one or more lumens, which may be used to pass one or more tools to a target site within a patient's body. Such tools may be used in conjunction with injector 116. As will be described in further detail below, upon lifting mucosal layers 10, including at least urothelial 50, from submucosal layer 20 the lifted tissue may be dissected, i.e., cut and removed from remaining tissue portions via a tool. By way of non-limiting examples, such tools may include hook 118 (FIG. 2B), snare 120 (FIG. 2C), and surgical blade 122 (FIG. 2D) and may include the use of energy, such as RF or laser energy or vibration. Each of such tools may include a portion configured to cut, incise, or otherwise dissect the lifted urothelilal 50 or mucosal layers 10. As such, each tool may include a sharpened or cutting portion capable of dissecting tissue. Further, each tool may be configured as an electrosurgery device. For example, each tool may be connected to a source of RF, laser, or microwave energy so as to dissect tissue via cauterization. The underlying injected hydrogel/polymer scaffold may promote the detrusor remaining intact during the process of tissue resection or thermal ablation.

Figure 3:
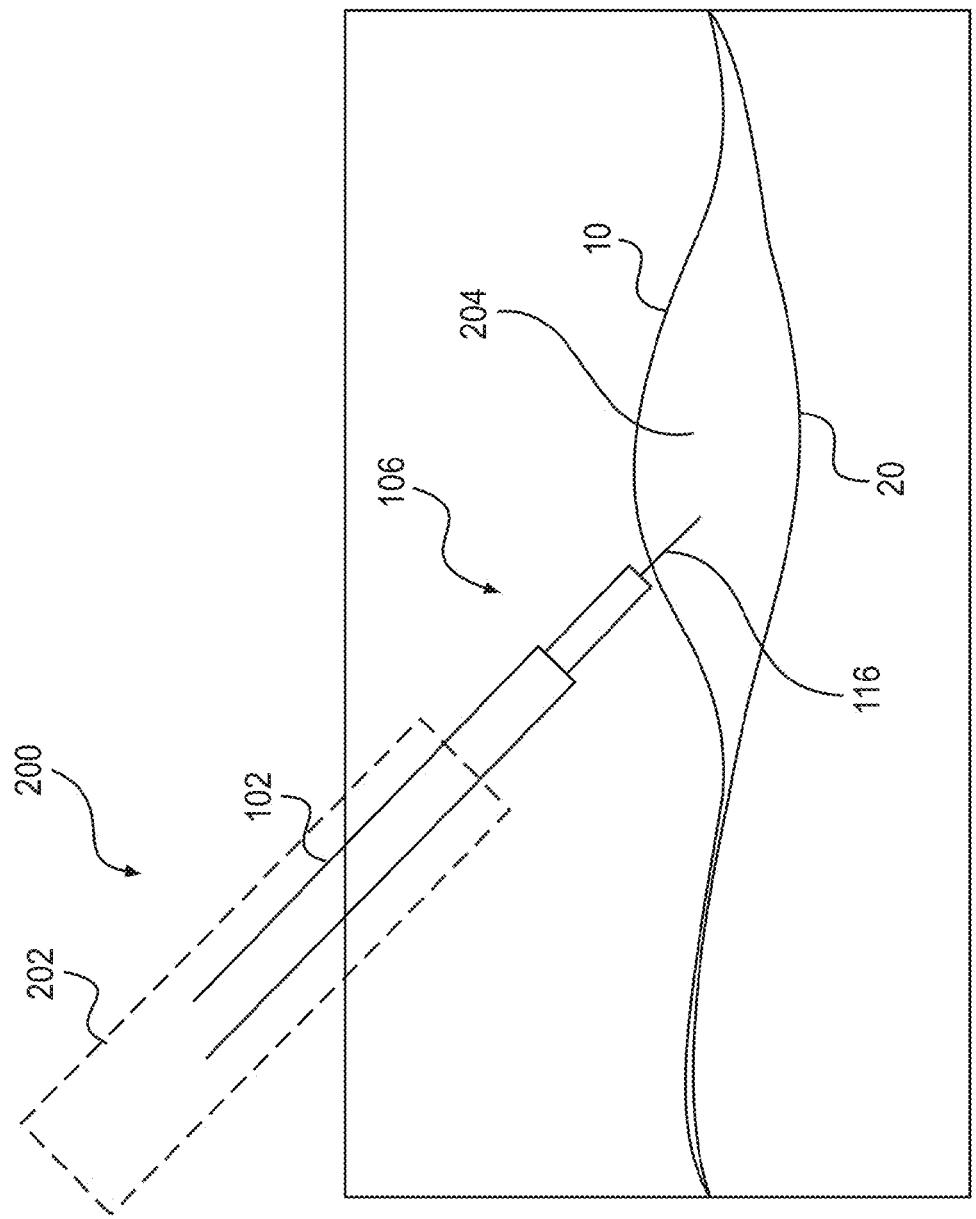
FIG. 3 is a schematic view of an exemplary method for separating tissue layers utilizing the medical device of FIG. 2A.

FIG. 3 is a schematic view of an exemplary method for separating layers in mucosal 10 and submucosal 20 regions of the bladder wall, illustrating an embodiment of the present disclosure. The disclosed method will be described as applied to treatment of a bladder. Those of skill in the art, however, will readily recognize that the principles of the disclosed embodiments may have utility relative to any organ within a patient's body. It will be further noted that both FIG. 3 and the discussion that follows below use like reference numbers to refer to elements of medical device 100 shown in FIGS. 2A-2D. Specifically, the illustrated embodiment of the present disclosure employs a medical device 200, which may be any suitable introducer, for example, an endoscopic device or a guide catheter.

The method illustrated in FIG. 3 includes injecting a substance, for example, an inert fluid or gel, between mucosal layer 10 (e.g., urothelium 50 and/or lamina propria 60) and submucosal layer 20 of the bladder wall. For example, the method may include injecting a substance between an outermost surface of mucosal layer 10 and an innermost surface of the submucosal layer 20. This method calls for inserting catheter 202 into the patient's urethra and extending the distal end of elongate tube 102 into the bladder. Catheter 202 may be inserted via, for instance, an endoscope, cystoscope, or any other suitable introducer. Using appropriate visualization means, the physician can identify a site of interest 204, where the injection is to occur. As mentioned above, the site of interest 204 may be a previously or simultaneously identified location exhibiting abnormal activity or morphology. Injector device 106 may be extended distally from elongate tube 102, exposing injector 116. This configuration of medical device 200 may be referred to as an "operating state" in which the device is prepared to perform the injection. Previously, injector device 106 and injector 116 are retracted within elongate tube 102, permitting elongate tube 102 to be advanced through the urethra and into the bladder without damaging adjacent tissues. The process of extending injector device 106 into the operating state is well known in the art and need not be discussed here.

The procedure continues with the physician advancing injector 116 to pierce mucosal layer 10, employing either manual control or visualizing techniques. In some embodiments, mucosal layer 10 may include the detrusor muscle layer as well. Mucosal layer 10 depth may be monitored in a number of ways. For example, the injection needle may be a single, predetermined length. Alternatively, the needle may be provided with radiopaque markers that can be visualized as the needle is penetrating tissue, or the needle itself may comprise radiopaque materials. In another embodiment, the device may be provided with a ratchet-like advancing mechanism, wherein the operator may be able to selectively advance the needle in known increments. In further embodiments, advancement of the needle may be monitored by ultrasound.

Once the distal tip of injector 116 reaches a site of interest 204, medical device 200 is actuated to inject a substance, for instance, an inert, non-toxic compound, between submucosal layer 20 and mucosal layer 10. The substance may include a liquid (e.g., saline), a gel, a liquid/gel that cures into a solid, a foam, or any other suitable porous material, for example. For example, the substance may include a hydrogel (e.g., PEG, hyaluronic acid, polyacrylamide gel, chitosan, sodium alginate, PLA, or hyrdrogel mixture), which, after injection, may be cured by cross-linking. In some embodiments, the substance may include a carrier or solvent that is later absorbed.

As shown in FIG. 3, the substance may serve to separate and maintain the two layers, reducing signal transduction between mucosal layer 10 and submucosal layer 20. This separation may create a semi-permanent barrier between submucosal layer 20 and mucosal layer 10 and may decrease signal transduction, decreasing both detrusor muscle 30 contraction and expansion. That is, in some embodiments, physical separation of submucosal layer 20 and mucosal layer 10 may result in decreased diffusion of compounds (i.e. agents) therebetween. Such substances may include, for example, adenosine triphosphate (ATP), prostaglandin, nitric acid (NO), and acetycholine (Ach). Additionally, the injected substance may have any desired composition, viscosity, and/or biodegradability characteristics so as to permit the injected substance, such as a cured hydrogel, to carry and deliver a drug over an extended period of time, for example, several months or years. Further, the injected substance, such as a hydrogel, may include high expansion properties (e.g., expanding between approximately five to approximately ten times its original volumetric size). As such, a large physical barrier may be achieved while using a small volume/amount of the injected compound. Additionally, such a hydrogel may be absorbable into the bladder wall.

After the injection is complete, the physician may retract injector device 106 to its non-operating state within catheter 202. The physician may then move the distal tip of medical device 200 to a second site of interest and perform a further injection, or medical device 200 can be withdrawn from the patient's body. That is, multiple injections, for example, approximately ten to approximately forty injections, may be performed. In some embodiments, each of such injections may be performed at sites of interest spaced equidistantly from one another along the bladder wall. Alternatively, the sites of interest need not be spaced equidistantly.

As noted above, an injected hydrogel compound may be cross-linkable. That is, ultraviolet light may be directed toward the injected substance to cure or otherwise cross-link the substance, thereby providing longer lasting physical separation between mucosal layer 10 and submucosal layer 20. Ultraviolet light may be directed toward the injected substance via introduction of an optical fiber-based light source advanced into the bladder transurethrally. Alternatively, any other appropriate ultraviolet light sources and/or introduction methods may be employed without departing from the scope of the disclosed embodiments. Other cross-linking substances may include heat, light, radiation, chemicals, or any other suitable agents.

In some embodiments, medical device 200 may include a suction device to assist in lifting mucosal layer 10 of the bladder wall. Further, device 200 may be capable of providing multiple injections with either a single injector or multiple injectors at either the same location or different locations.

Following separation of mucosal layer 10 from submucosal layer 20, one or more tools, such as hook 118, snare 120, and blade 122, may be optionally advanced though medical device 200 to reach site of interest 204. In some embodiments, multiple tools may be combined into one, universal tool. For instance, a needle and a snare may be incorporated into one device. In an embodiment in which snare 120 is used, snare 120 may be positioned such that the loop of snare 120 surrounds injector 116. In such an exemplary embodiment, as injector 116 is withdrawn after having injected the substance, snare 120 may hook around and dissect the lifted tissue. Upon reaching site of interest 204, hook 118, snare 120, and/or blade 122 may be manipulated so as to dissect the separated mucosal layer 10. That is, such tools may be used to cut or incise mucosal layer 10 so as to allow removal of the portion lifted from submucosal layer 20.

In an embodiment in which a cross-linked hydrogel is utilized as the injection substance, the cross-linked hydrogel may serve as a scaffold for tissue, such as mucosal layer 10 tissue, overgrowth. Indeed, the hydrogel may be considered "active" and may contain seed cells, drugs, agents, or the like to promote proper healing of site of interest 204. Substances may be injected separately and/or simultaneously, for instance, cells may be injected separately or simultaneously, or different types of agents may be injected separately or simultaneously. The active hydrogel or other substance injected may bind, lyse, or otherwise render chemicals, such as, for example, ACH and ATP, which are released in response to urine and bladder stretch, ineffective. The injected substance may also include multiple drugs, for example, a first drug may be configured to elute from the injected substance quickly to promote tissue healing and regrowth, whereas a second drug may be configured to elute slowly (over several months or years) to inhibit transmission between receptors and nerves. Examples of such drugs may include, for example, anticholinergic, imipramine, desmopressin, estrogens, botulinum toxin, intravesical vanilloids (capsaicin, resiniferatoxin), lidocain, etc. In place of drugs, the hydrogel may contain compounds that bind or degrade acetycholine or ATP, such as, for example, the enzyme acetylcholinesterase, which degrades acetylcholine. To degrade ATP by hydrolysis, the hydrogel may contain enzyme ATP-ase and water, or it may contain salts of ions, such as Mg2+, that may trap the hydrolyzed ATP. Furthermore, the scaffold may also help the detrusor muscle to remain intact during the process of tissue resection or thermal ablation. Upon dissection of the lifted tissue, the site may be allowed to heal, i.e., healthy tissue may grow over the area in which the lifted tissue has been removed.

The description above contemplates a primarily manual operation of the disclosed method. As known in the art, however, a number of automation techniques may be applied to improve control and accuracy of the process. For example, the exact positioning and depth of penetration may be monitored by appropriate visualization technology, or the penetration itself can be carried out under computer control.

The substance to be injected in the disclosed method can be selected from among suitable inert or active compounds, which can be configured as, e.g., a fluid or gel, suitable for injection. For example, the substance may be saline solution. However, any biocompatible liquid, gel, or curable material may be used. In some embodiments, substances may be injected separately and may interact once injected to create a desired effect.

Figure 4:
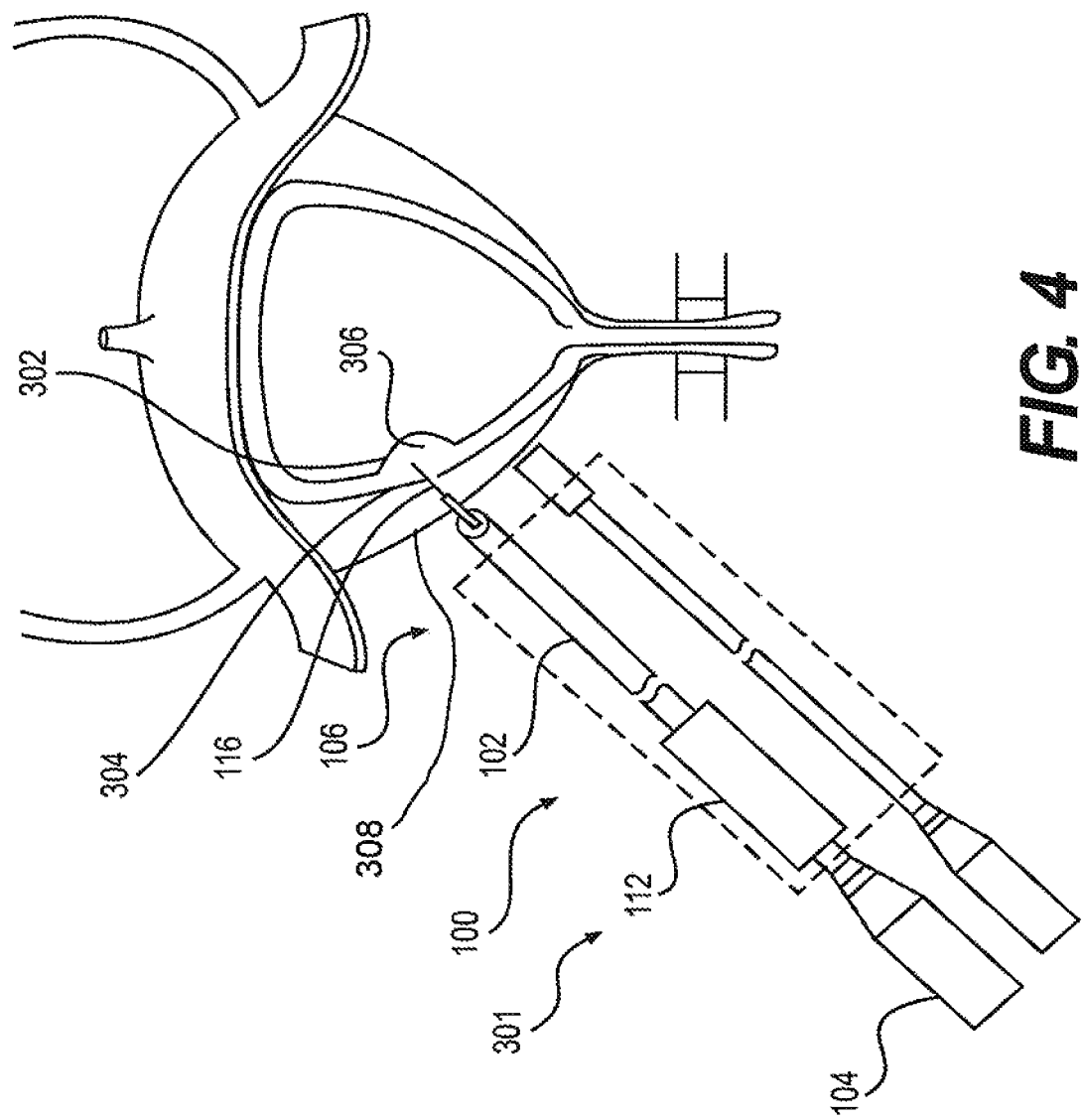
FIG. 4 is a schematic view of an exemplary method for treating an overactive bladder by separating tissue layers, according to another embodiment of the present disclosure.

FIG. 4 illustrates an alternative approach to advancing the distal tip of medical device 100 into position to perform the required injection. An operator may bring medical device 100 into position by employing a body lumen, such as the urethra. In some conditions, that method may be termed an "inside-out" approach, as the bladder wall is approached from inside the bladder. In some conditions, a physician may determine that a better approach would be to operate from "outside-in," bringing injector element 106 into position from outside the bladder, as illustrated in FIG. 4.

As illustrated there, laparoscopic surgical techniques may be employed to introduce a device, such as an endoscope 301, into the lower pelvic area and to bring the distal portion of endoscope 301 into a selected position adjacent the bladder wall. Alternative surgical approaches to position endoscope 301 adjacent the bladder wall will be apparent to those skilled in the art. In addition, the contemplated method may be utilized with other organs throughout a patient's body.

Once in position, injector 116 may be actuated by handle 104 to pierce the bladder wall. In another embodiment, suction may be applied to pull tissue towards the device or to make the tissue taut for piercing the bladder wall. Injector 116 may pierce the bladder wall and traverse detrusor muscle layer 308 in an outside-in direction to a desired depth, operating under manual or computer control. The injected substance 306 may physically separate submucosal layer 302 and urothelium layer 304, decreasing signal transduction to eliminate the detrusor contractions that may characterize OAB. The substance insertion between the submucosal and urothelium layers may be performed at multiple locations of the bladder wall. Further, the procedure may be repeated periodically depending upon the chemical nature of injected substance 306. As would be understood by a person of ordinary skill in the art, any other method for dispensing substances may be employed for delivering a substance to injector 116. Once urothelium 304 and submucosal 302 layers are physically separated, injector device 106 is removed from the bladder wall.

A control mechanism may operate injector 116 either manually or automatically. For example, a physician may monitor the treatment location, detrusor muscle 302 depth, and amount of substance to be injected between submucosal 302 and urothelium layer 304 in the targeted area of the bladder wall via an endoscope 301. Alternatively, the control mechanism may automatically insert medical device 100 into a human body, penetrating the bladder wall to deliver a substance, e.g., a liquid or gel, under computer control, as would be understood by a person skilled in the art. In automated embodiments, parameters may be provided as a set of instructions to a processor, which in turn, may automatically control injector 116 to pierce the bladder wall to a desired depth and inject the requisite amount of substance 306 to the bladder wall's targeted location.

As mentioned above, injected substance 306 may be an inert fluid, such as saline solution, a biocompatible gel, or a pharmaceutical compound, for example. In some embodiments, injected substance 306 may be a therapeutic solution or may be used as a marker. That is, the substance may be a contrast or dye visible with suitable imaging techniques. Moreover, it would be understood by one skilled in the art that any other non-toxic, inert substance might be utilized for separating urothelium 304 and submucosal 302 layers of the urinary bladder wall.

Figure 5:
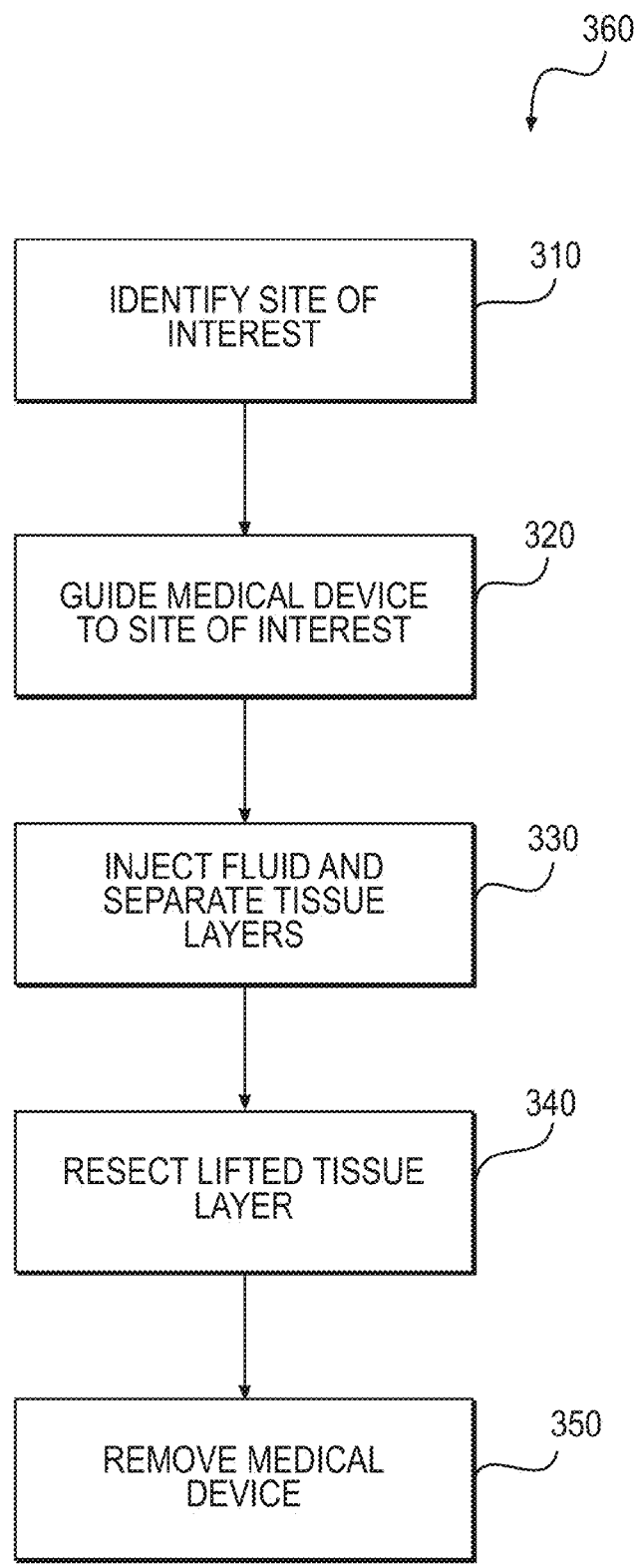
FIG. 5 is a flowchart of an exemplary method for treating an overactive bladder, according to an embodiment of the present disclosure.

FIG. 5 illustrates a schematic flow diagram of the disclosed methods and procedures for treating a condition, such as, for example, OAB. As shown, method 360 may include identification of site of interest 204 at step 310. Identification may be performed, as noted above, under appropriate visualization means. Site of interest 204 may be a previously or simultaneously identified location exhibiting abnormal activity or morphology. At step 320, method 360 may include guiding medical device 100, 200, to site of interest 204. As noted above, a medical device may be guided under appropriate visualization means and may be positioned at the site of interest via access through the urethra. Alternatively, other known approaches, such as laparoscopic positioning of a medical device, may be utilized.

At step 330, method 360 includes injection of a substance, for example, a fluid (such as e.g., a hydrogel), to separate tissue layers. That is, a substance, such as saline or a similar inert liquid or gel, may be injected into a position between mucosal layer 10 and submucosal layer 20 so as to reduce signal transduction, thereby modifying detrusor muscle 30 contraction and lifting submucosal layer 20. After lifting submucosal layer 20, method 360 optionally includes the step of resecting, i.e., incising and removing, the lifted tissue layer at step 340. Following resection, the procedure may be repeated at various locations, i.e., varying sites of interest 204, and then removed when completed at step 350. After completion of method 360, the removed tissue portions may be permitted to heal, i.e., healthy tissue may be permitted to grow in the area of the optionally removed tissue.

It should be understood that the methods according to the present disclosure present improvements to the treatment of overactive bladder. For example, embodiments of the present application recognize the need for localized treatment of specific areas via lifting and optionally resecting rather than treatment of the entire organ. As such, contrary to prior methods of treating the bladder in its entirety, the method according to the present disclosure treats abnormal tissue, allowing a focused approach to treating unhealthy tissue within a bladder. This approach may also be used to remodel part of the bladder wall for bladder cancer and interstitial cystitis as an alternative to more invasive bladder augmentation. If cancer is located in the mucosal region, the mucosal liftoff and removal may allow the physician to keep the underlying detrusor intact while providing a substance, such as a hydrogel scaffold, for potentially faster regrowth of mucosa (potentially resulting in faster recovery times and lower post-op morbidity).

It should be apparent that the medical device of the present disclosure may be used to carry out a variety of medical or non-medical procedures, including surgical and diagnostic procedures, in a wide variety of body locations. For example, mucosal resection or ablation of a variety of body organs, such as the esophagus, stomach, bladder, or urethra, could be accomplished using the method discussed above. In addition, at least certain aspects of the aforementioned embodiments may be combined with other aspects of the embodiments, or may be removed without departing from the scope of the disclosure.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the claims are not to be considered as limited by the foregoing description.

What is claimed is:

1. A method of treatment, comprising:
advancing a medical device to a wall of an organ of a patient, the wall having a plurality of layers of tissue including, from inside out, a first layer, a second layer, and a third layer containing a muscle, wherein the medical device comprises:
an elongate tube having a proximal end and a distal end and a lumen extending therebetween; and
an injector disposed within the lumen of the elongate tube, the injector being configured to deliver a substance to one of a plurality of locations within the wall,
wherein each of the plurality of locations is disposed between an innermost surface of the first layer and an outermost surface of the second layer, the first layer being a mucosal layer of the organ, the second layer being a submucosal layer of the organ; and
delivering the substance to the plurality of locations to maintain a spatial separation between the first and second layers that modifies contraction of the muscle by inhibiting signal transduction for at least one month, wherein at least two of the plurality locations are discontinuous with one another.

2. The method of claim 1, further including:
resecting a portion of at least one of the first and second layers of tissue with a resection tool.

3. The method of claim 1, further including:
extending the injector out of the lumen of the elongate tube, wherein the injector is configured to pierce the organ wall.

4. The method of claim 1, further including:
applying suction to one of the first and second layers of tissue.

5. The method of claim 1, wherein the organ is a bladder and the muscle is a detrusor muscle.

6. The method of claim 1, wherein the first and second layers include nerves, the second layer including a greater number of nerves than the first layer, and the first layer further includes one of a muscarinic and cholinergic receptor.

7. The method of claim 1, wherein the method further includes identifying a location of abnormality on the organ wall.

8. The method of claim 1, wherein the substance is a fluid configured to cure into a solid.

9. The method of claim 8, wherein the substance includes a hydrogel.

10. The method of claim 1, wherein the substance is configured to deliver a drug over a period of time.

11. A method of treating a wall of a bladder, the wall having plurality of layers including, from inside out, a first layer, a second layer, and a third layer containing a muscle, the method comprising:
  positioning a distal end of a medical device adjacent to the wall of the bladder, the medical device comprising:
    an elongate tube having a proximal end, a distal end, and a lumen extending therebetween; and
    an injector disposed within the lumen of the elongate tube, the injector including a needle configured to pierce the wall;
  advancing the injector to a plurality of locations within the wall; and
  delivering a substance between an innermost surface of the first layer and an outermost surface of the second layer at each of the plurality of locations,
  wherein the first layer is a mucosal layer of the bladder and the second layer is a submucosal layer of the bladder,
  wherein, when delivered, the substance is configured to semi-permanently maintain a spatial separation between the first and second layers that modifies contraction of the muscle by inhibiting signal transduction for at least one month,
  wherein at least two of the plurality locations are discrete from one another.

12. The method of claim 11, further including:
  resecting a portion of at least one of the first and second layers of the wall of the bladder with a resection tool.

13. The method of claim 12, wherein the resection tool includes at least one of a hook, a snare, and a surgical blade.

14. The method of claim 11, further including:
  applying suction to one of the first and second layers.

15. A method of treating a wall of a bladder, the wall having a plurality of layers of tissue including, from inside out, a first layer, a second layer, and a third layer containing a detrusor muscle, the method comprising:
  positioning a distal end of a medical device adjacent to an anatomical area of the wall, the medical device comprising:
    an elongate tube having a proximal end and a distal end and a lumen extending therebetween; and
    an injector disposed within the lumen of the elongate tube, the injector including a needle configured to pierce the wall; and
  advancing the injector to a plurality of locations within the wall at the anatomical area and delivering a substance to each of the plurality of locations,
  wherein each of the plurality of locations is between an innermost surface of the first layer and an outermost surface of the second layer,
  wherein the first layer is a urothelium and, the second layer is a lamina propria, and the anatomical area includes one of a dome, an internal sphincter, or a trigone,
  wherein, when delivered, the substance is configured to maintain a spatial separation between the first and second layers that modifies contraction of the detrusor muscle by inhibiting signal transduction for at least one month, and
  wherein at least two of the plurality locations are discontinuous with one another.

16. The method of claim 15, wherein the substance includes a hydrogel.

17. The method of claim 15, wherein each of the plurality locations is discontinuous with one another, further including:
  repositioning the distal end of the medical device before delivering the substance to each of the plurality of locations.

* * * * *